United States Patent [19]

Brous

[11] Patent Number: 4,486,303

[45] Date of Patent: Dec. 4, 1984

[54] ULTRAFILTRATION IN HEMODIALYSIS

[76] Inventor: Donald W. Brous, 110 Hunt, Peterborough, N.H. 03458

[21] Appl. No.: 482,141

[22] Filed: Apr. 5, 1983

Related U.S. Application Data

[63] Continuation-in-part of Ser. No. 308,985, Oct. 6, 1981, abandoned.

[51] Int. Cl.³ ............................................. B01D 31/00
[52] U.S. Cl. .................................. 210/87; 210/321.3; 210/929
[58] Field of Search ............. 210/87, 929, 646, 321.3, 210/321.2

[56] References Cited

U.S. PATENT DOCUMENTS 3,946,731  3/1976  Lichtenstein ................... 210/929 X Primary Examiner—Frank Spear
Attorney, Agent, or Firm—Charles R. Fay

[57] ABSTRACT

Control of ultrafiltration by the use of two flowmeters which include fluid flow controls, one between the dialysate supply and the dialyzer input, and a second such flowmeter between the dialyzer output and the effluent. Alternatively, a smaller capacity flowmeter may be placed in parallel with the output flowmeter, to be read as a "vernier".

2 Claims, 4 Drawing Figures

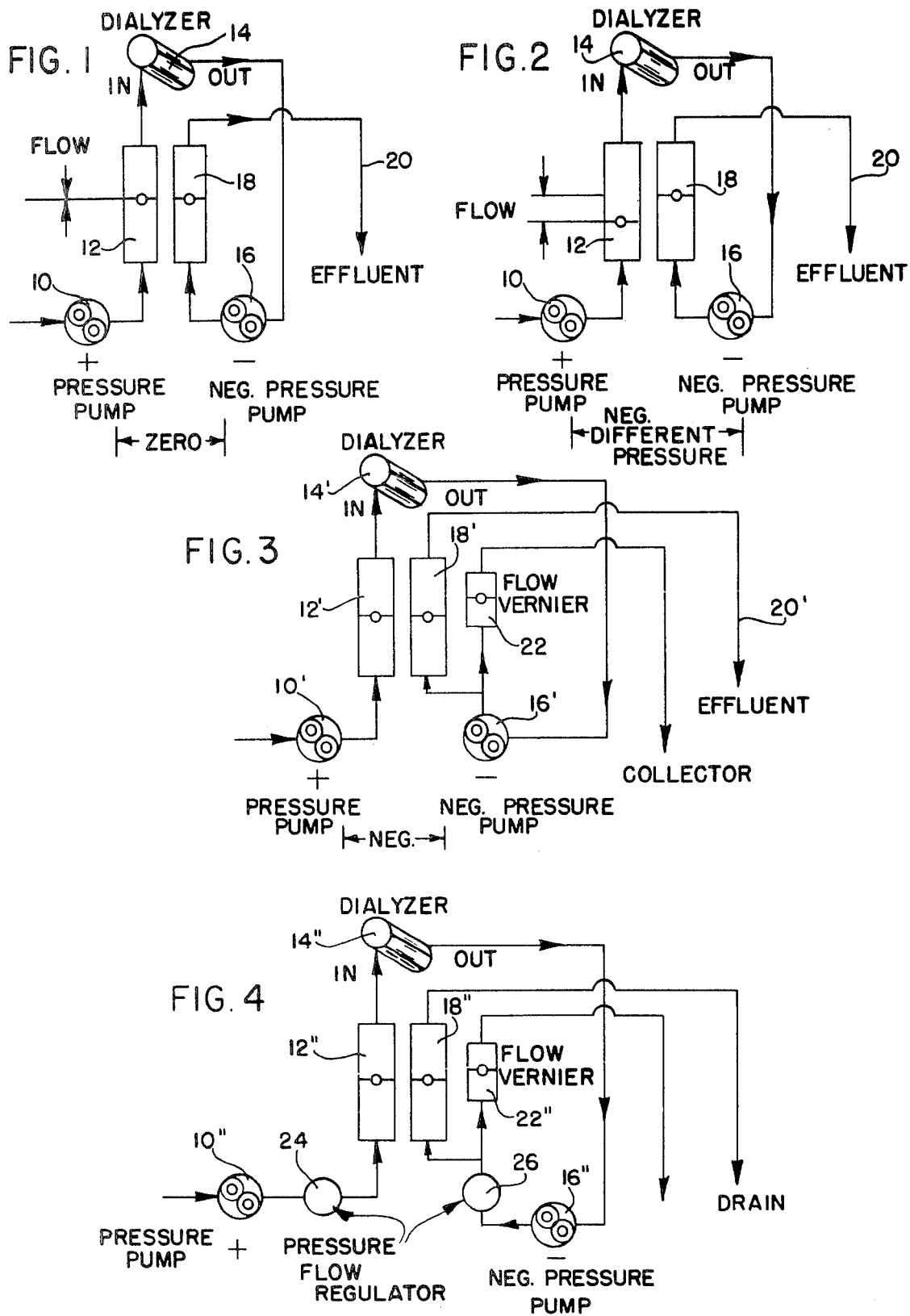

ULTRAFILTRATION IN HEMODIALYSIS

This application is a continuation-in-part of Ser. No. 308,985, filed Oct. 6, 1981, now abandoned.

FIELD OF THE INVENTION

Measurement and control of ultrafiltration in dialysis.

BACKGROUND OF THE INVENTION

There are several extant methods and apparatus for the measurement of ultrafiltration in hemodialysis. The principal ones are as follows:

I—Extracorporeal

Uses special negative pressure dialyzer (hollow fiber).

Each dialyzer (single use) incorporates chambers and ducts with a 100 ml/hr. to 700 ml/hr. scale. The technique requires:

(1) inverting the dialyzer while the patient is "on"; (2) stopping dialysate flow; (3) injecting air into the dialyzer; (4) waiting for dialyzer pressure to stabilize; (5) returning dialyzer to original position; (6) timing the refilling of the internal duct in the dialyzer by stop watch for exactly 60 seconds; (7) reestablishing dialysate flow; (8) clearing air from dialyzer by rotating it.

Disadvantages: (1) injecting air; (2) special dialyzer; (3) split-second timing; (4) cessation of dialysis during the "reading"; (5) reading indicates intermittent ultrafiltration during 60-second period only—not for entire dialysis time, not even for several minutes. It is an instantaneous value which may or may not represent the average ultrafiltration.

Operator care and skill are all important.

II—Travenol—negative pressure type

Provides arterial and venous pressure, and dialysate pressure, gauges only—Transmembrance Pressure (TMP) must be calculated, including use of a permeability factor for the dialyzer.

Disadvantages: (1) accuracy highly questionable; (2) complicated mathematical calculations discouraging to the user, and results not predictably precise or reproducible; (3) dialyzer variability is unknown factor. Operator care and skill are all important.

III—Travenol—coil type

The Monitor consists of a vessel to house the coil dialyzer and to plug into the canister, with a rachet mechanism to raise and lower the coil manually. During ultrafiltration measurement, and rachet is manually actuated to position the coil out of the normal dialysate perfusion circuit by valves. The ultrafiltrate then causes excess fluid to fill a sampling tube in the monitor. This is timed by stop watch and the amount accumulated translated into ml/hr. by a conversion chart.

Disadvantages: (1) split-second timing; (2) cessation of dialysis during measurement; (3) reading indicates instantaneous value, which may not be representative of ultrafiltration rate over longer periods. Operator still all-important.

IV—Drake Willock—negative pressure dialyzer only

This is a complex instrumentation system which "predicts" rate of ultrafiltration. Instruments measure the arterial pressure, the venous pressure, and the dialysate pressures to and from the dialyzer. These four values are computed by electronics to determine the Transmembrane Pressure (TMP). An arbitrary member, called the dialyzer's "Ultrafiltration Index", is then factored in, and a calculated result is called the UFR or Ultrafiltration Rate.

Disadvantages: Complex instrumentation which is capable only of instantaneous values, and subject to gross errors of the dialyzer's "Index".

The manufacturer lists the following "several variables that can affect fluid removal. These should always be considered in assessing ultrafiltration: (1) Accuracy of the method for measuring patient weight before and after dialysis; (2) Fluid inputs and losses during priming, dialysis, and rinse back; (3) Solid and liquid food intake during dialysis; (4) Osmolality of the dialysate and blood; (5) The electrolyte balance of the patient; (6) Blood and dialysate flow rates during dialysis; (7) Variations in dialyzer membrane characteristics (the UF Index), and (8) Clinical status affecting insensible loss".

The circuit of the current invention splits off the ultrafiltrate from effluent, through a vernier bypass, AFTER the downstream pump—on the positive pressure output of the negative pressure downstream pump.

The state-of-the-art today employs accurate stopwatch timing to determine the volume extracted in a precise interval, when dialysis has been temporarily bypassed; or mathematical calculations of transmembrane pressure (4 measurements) and a factor representing the dialyzer's estimated filtration characteristics. This calculation is performed electronically in some cases, or multiplied out by staff or patient in others.

SUMMARY OF THE INVENTION

The present method of measuring and controlling ultrafiltration is very direct and simple.

First, the flow of dialysate into the dialyzer is controlled precisely, by placing an in-flow control meter with needle valve and a pressure regulator between the dialysate supply and the dialyzer input. This results in accurate, adjustable inflow rate that is independent of the pressure of the dialysate supply.

From the output of the dialyzer, the effluent is directed into a negative pressure pump. The output of this pump then passes through a pressure regulator and output flow control meter. This output flow meter is capable of controlling and displaying a greater flow than the input flow meter and regulator. At zero negative pressure, this flow meter will read exactly the same as the input flow meter. As the negative pressure is increased, the ultrafiltrate fluid removed from the patient will be shown as an increase in output flow rate. The output flow meter can be calibrated in engineering units, e.g. Kg/hr.

An alternative method places a smaller capacity flow and control meter in parallel with the output flow and control meter, to be read as a "vernier". In this mode, the output flow meter and regulator is adjusted to exactly the same rate of flow as the input flow meter, at zero negative pressure. As the negative pressure is increased, the output flow meter remains constant and the excess or ultrafiltrate flows through the vernier flow meter and is observed.

Alternatively, the effluent flow meter and the vernier flow meter can be on the vacuum or inlet side of the negative pressure pump.

The significant measurement here is the excess of ultrafiltrate. It can be displayed by a conventional glass tube—float flow meter; or by a transducer with either digital or analog display. The engineering units may be g/m or Kg/hr. rather than cc/min.

The basic input flow may be 500 cc/min. as is most frequently employed, or it can be whatever value is desired. The only requirement is that the output flow is exactly the same, at zero negative pressure.

In addition to reading continuously and directly the rate of fluid extracted in this invention, by storing up the excess fluid in a vessel, the total ultrafiltration can be seen and accurately determined or alternatively electronically totaled and read out. When analog or digital flow meters with transducers are employed, an electrical output signal can be read directly or employed to drive, e.g., a strip chart recorder or printout for recording ultrafiltrate rate and to integrate the volume extracted.

BRIEF DESCRIPTION OF THE DRAWING

FIG. 1 is a diagram illustrating a flow meter dialyzer arrangement wherein there is zero pressure drop accross the dialyzer membrane;

FIG. 2 is the same diagram but showing a negative pressure drop;

FIG. 3 is a similar diagram with the addition of a vernier flow meter;

FIG. 4 is a diagram similar to that of FIG. 3 with the addition of pressure or flow regulators.

PREFERRED EMBODIMENT OF THE INVENTION

FIG. 1 shows an "in" pressure pump of well-known design at 10, which provides flow during dialysis through a flow meter and control 12 to the dialyzer 14, to the "out" side, a second pressure pump 16, flow meter and control 18, to effluent at 20. In FIG. 1, the flowmeters are clearly visibly equal, hence there is no pressure drop across the dialyzer, and flow "in" is equal to flow "out" and no fluid is extracted from the patient. However, when negative pressure is applied to the effluent, more flow is created "out" than "in". The delta is the fluid extracted from the blood of the patient as by the differential pressure across the dialyzer membrane, FIG. 2. Conversely, should "out" by e.g. partially occluded and a positive pressure applied to the dialyzer, a very undesirable condition is shown by the flow meter to exist, wherein fluid is put into the patient.

As so far described, the invention is in its simplest form and is based on the two flow and control meters that indicate the ultrafiltration rate, and are easily manually adjustable for the benefit of the patient. Such flow and control devices are manufactured and sold by several concerns; i.e., Pennwalt, Porter Instrument Co., Hoffer Flow Controls, Inc., Kurz Instruments Inc., et al.

Referring to FIG. 3, a "vernier" 22 is placed in parallel with flow meter 18. This vernier may be an optional magnifier to provide for reading the difference in flow directly, or it may be a lower-flow flowmeter in a T or Y connection in the output. In the latter case, the two main flow meters 12, 18' are manually adjusted to read identically, and the differential output is read on the auxilliary low-flow flowmeter 22.

For example: The two flowmeters 12 and 18 are locked in at, say, 500 cc/min. each. The vernier flowmeter 22 regulator is adjusted for zero flow at zero negative pressure. No ultrafiltration is being exerted. Adjusting the negative pressure to produce an ultrafiltration of, say, 10 cc/min. with 12 and 18 still at 500 cc/min., a total of 600 cc/hr. is now being removed from the patient and will be so indicated on the vernier 22 as 10 cc/min. (or whatever scale calibration is desired, such as KG/hr.).

FIG. 4 shows a situation similar to that in FIG. 3, with the addition of a pressure flow regulator 24 controlling the flow of the input pump 10". This provides an exact, constant flow rate, and by using another flow regulator 26 in the output, after pump 16", any need for manual adjustment during a "run" is completely eliminated.

All parts of this invention are commercially available.

The preferred embodiment would display the delta flowmeter to show ultrafiltration, and automatic input and output controls. The total flow could be displayed but only as safety instrumentation.

Integration of this delta flow could be accomplished by mechanical or electronic totalizers or, more simply, by collecting the delta effluent in a calibrated carboy—say ten liters maximum—and simply measuring the volume after the run.

The instrumentation for control, however, is from the cc/min. flow indication of the delta readout. Only this will give patient or staff an accurate and safe manner of setting proper ultrafiltration rate.

The total accumulated is only a check. It is after the fact, of historical interest, to be entered in the patient's clinical records.

A scanner, proximity detector or similar device, may be added to the vernier flow meter for the purposes of alarm, should there be a deviation from the desired rate of ultrafiltration.

I claim:

1. Hemodialysis apparatus including a dialyzer and input and output pumps therefor,
    a first flow meter and control means operatively located between the input pump and the dialyzer, and a second flow meter and control means operatively located after the output pump and dialyzer,
    said first and second flow meter means each being adjustable for controlling the passage of fluid therethrough at a selected flow rate, and each having means for indicating the flow rate of fluid passing therethrough,
    a first pressure flow regulator means operatively located between said input pump and said first adjustable flow meter to regulate the flow of the input pump, and a second pressure flow regulator means operatively located between said output pump and said second adjustable flow meter to regulate the flow of the output pump,
    said first and second flow meter and control means normally being adjusted for equal flow rates.

2. Hemodialysis apparatus including a dialyzer and input and output pumps therefor,
    a first flow meter and control means operatively located between the input pump and the dialyzer, and a second flow meter and control means operatively located after the output pump and dialyzer,
    said first and second flow meter means each being adjustable for controlling the passage of fluid therethrough at a selected flow rate, and each having means for indicating the flow rate of fluid passing therethrough, a vernier flow meter of lesser capacity than said second flow meter located in parallel with the output flow meter and receiving effluent from said output pump, a first pressure flow regulator means operatively located between said input pump and said first adjustable flow meter to regulate the flow of the input pump, and a second pressure flow regulator means operatively located between said output pump and said second adjustable flowmeter to regulate the flow of the output pump, said first and second flow meter and control means normally being adjusted for equal flow rates whereby the vernier flow meter will measure the delta flow rate.

* * * * *